US00PP08517P

United States Patent [19]

Marionnet

[11] Patent Number: Plant 8,517

[45] Date of Patent: Dec. 28, 1993

[54] STRAWBERRY PLANT NAMED "MARA DES BOIS"

[75] Inventor: Andre Marionnet, Soings-en-Sologne, France

[73] Assignee: Jacques Marionnet G.F.A., Soings en Sologne, France

[21] Appl. No.: 760,265

[22] Filed: Sep. 16, 1991

[51] Int. Cl.[5] ..... A01H 5/00
[52] U.S. Cl. ..... Plt./49
[58] Field of Search ..... Plt./48, 49

[56] References Cited

U.S. PATENT DOCUMENTS

P.p. 7,566 6/1991 Hureau ..... Plt. 49

*Primary Examiner*—James R. Feyrer
*Assistant Examiner*—Erich Veitenheimer
*Attorney, Agent, or Firm*—Browdy and Neimark

[57] ABSTRACT

A new and distinct variety of strawberry denominated "Mara Des Bois" is the offspring of (Gento×Ostara)×(Red Gauntlet×Korona). It is a remontant variety but has strong Spring production, as well as the remarkable scent of wild strawberries.

2 Drawing Sheets

FIELD OF THE INVENTION

This invention relates to a new and distinct variety of strawberry denominated "MARA DES BOIS".

SUMMARY

The new strawberry of the present invention is a member of the species *Fragaria L.* and is the offspring of (Gento×Ostara)×(Red Gauntlet×Korona), and it is particularly notable and distinguished from its ancestors in the remarkable fragrance of its fruit which is similar to wild strawberries, and its unusually strong Spring production of fruit in spite of its remontance.

BRIEF DESCRIPTION OF THE DRAWING

FIG. 1 is closeup photograph of a bunch of fruit, including ripe fruit and unripe fruit;

FIG. 2 is a photograph taken further away than FIG. 1, showing leaves, flowers unripe fruit and ripe fruit.

DETAILED DESCRIPTION

Figure 3:
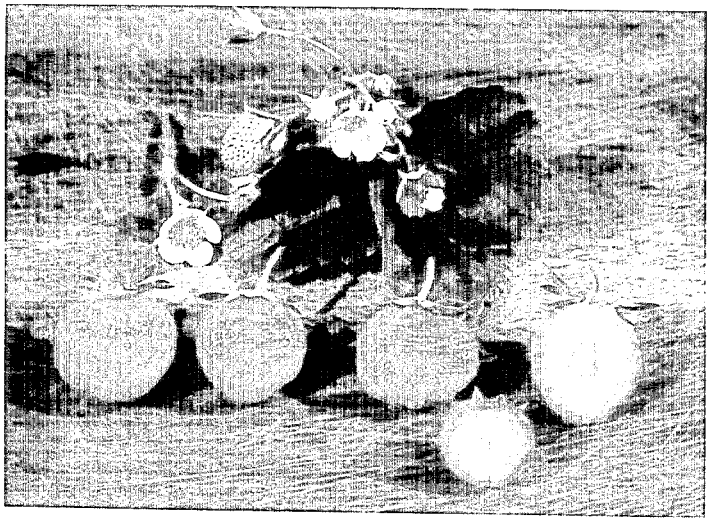
FIG. 3 is a closeup photograph showing leaves, flowers, three whole ripe fruit, a ripe fruit cut longitudinally and a ripe fruit cut horizontally.

The following detailed description provides various characteristics of the plant.

The present strawberry is particularly characterized in that it is fully remontant, but still with strong production in the Spring. In addition, the fruit has the remarkable fragrance of wild strawberries.

The new cultivar is a product of a planned breeding program which base objective was to create a new everbearing variety having good color, good shape, good productivity and mostly good taste.

The following observations, measurements and values describe plants grown in Soings En Sologne, France, under conditions which closely approximate those generally used in commercial practice.

Parents: (Gento×Ostara)×(Red Gauntlet×Korona).
Place of Crossing: Soings En Sologne - France.

The first selected plant was asexually propagated by tissue culturing from the cross. The specimens of the variety derived from this tissue culturing were then propagated in a nursery by the production of runners.

COMPARATIVE CHART:
(Observations in SOINGS EN SOLOGNE - FRANCE)
(Comparisons of
MARA DES BOIS with SELVA, FERN and MUIR)

| | SELVA | FERN | MUIR | MARA DES BOIS |
|---|---|---|---|---|
| PLANT VIGOR | medium | weak | medium | medium |
| LEAF HABIT | slightly flat | half upward | flat | flat |
| FRUIT | conical to cylindrical | change-able | cordate | conical |
| COLOR | orange-red to red | dark red | orange-red | orange-red |
| FRUITING PERIOD | ever-bearing | ever-bearing | ever-bearing | ever-bearing |
| PICKING DURATION | 4–6 months | 2–3 months | 4–6 months | 4–6 months |
| TOLERANCE TO PARASITES | slightly sensitive to oidium mycos-phaerella | slightly sensitive to oidium sensible to mycos-phaerella | sensitive to tetra-nychus urticae | goods tolerance to oidium phyto-phtora cactorum and mycos-phaerella |
| TASTE OF THE FRUIT | weak to very weak | medium | weak to medium | very strong taste |

YIELD CHART:

Date of Plantation: 04.08.1992
Last Removal of Flowers: End of May
Plastic Tunnel Installed: Early July

| VARIETY | DATE OF HARVEST Beginning | DATE OF HARVEST End | COMMERCIAL YIELD g/plant | AVERAGE WEIGH g/fruit |
|---|---|---|---|---|
| SELVA | 07/16 | 10/19 | 676 | 15.4 |
| MARA des BOIS | 07/16 | 10/19 | 768 | 11.20 |
| MUIR | 07/16 | 10/19 | 720 | 15.04 |

-continued

| | | | | |
|---|---|---|---|---|
| FERN | 07/16 | 10/19 | 465 | 11.75 |

FRUIT (A) Overall size and shape: medium size, similar to FERN, smaller than SELVA. Conical shape.

*Weight.*—11 to 16 gr. The secondary fruits are same shape as primary fruits, but a little smaller. At Soings En Sologne — France the harvest starts in May and ends at the end of October.

(B) Seed characteristics: Seeds show on the surface of the fruit.

(C) Juiciness: Medium.

(D) Taste: Taste and odor very strong with medium acidity.

(E) Color: Exterior: medium red to orange. No white zones near the peduncle. Red Group.46B of The Royal Horticultural Society Colour Chart.

(F) Exterior Surface (1) *Glossy.*—Not as strong as Selva.

(2) *Shape.*—Conical.

(3) *Firmness.*—Not as firm as Selva.

(G) Characteristics of flesh and core: Red-orange, more juicy than Selva.

(H) Keeping Qualities: Keeps its brilliance and firmness over three days at a temperature of 8° C. After cold storage, 2 to 3 hours are required to recover its initial fragrance. Its preserving is not as good as that of Selva. Its color becomes a little darker during cold storage.

(I) Time of ripening (50% plants): Medium.

(J) Fruit bearing habit: Everbearing.

(K) Fruiting truss: Attitude at first picking, prostrate.

(L) Fruit ratio of length/max width: Longer than broad.

(M) Predominant shape of fruit: Conical.

(N) Difference in shape between primary and secondary fruits: No difference, but the secondary fruits can be slightly smaller than primary fruits.

(O) Band without achenes (seed): Very small.

(P) Uniformity of fruit: Generally uniform, may contain slight clefts.

(Q) Uniformity of color: Even.

(R) Glossiness: Strong.

(S) Insertion of achenes (seeds): Show on the surface.

(T) Insertion of calyx: Overhanging.

(U) Position of the calyx segments: Misattached.

(V) Size of calyx in relation to fruit diameter: Smaller (W) Adherence of calyx: Medium.

(X) Aroma: Very fragrant and tasty fruit. Taste and odor are similar to wild strawberry. Fruits are most tasty when maturing and harvesting occur during warm weather. At the end of the crop (October), taste becomes weaker but stands much higher than that of Selva.

Disease tolerant: Resistant to oidium, mildly sensitive to phytophtora cactorum.

General observation: Behaving such as most of the everbearing varieties. Its best feature is its remarkable taste and odor quality.

The fruit size is medium comparable to the variety Tigaiga, and the predominant shape is conical comparable to the varieties Gorella and Talisman more conical than those of Selva. Its color, which is not a distinctive characteristic of the variety, is red/brick red comparable to the varieties Royal Sovereign and Precosa lighter than those of Selva. Its achenes are level with its surface comparable to the variety Regina.

The fruits of Mara De Bois are not as firm as those of Selva. The size of the fruits are slightly smaller than those of Selva. They are also more brilliant than Selva. Mara Des Bois contains high quantities of sugar whereas Selva contains low quantities. The acidity of Selva fruit is weak, whereas the acidity of Mara Des Bois is medium.

Time of fruit ripening; the time of ripening (50% of plants with ripe fruits) is medium, comparable to the varieties Cambridge Favorite and Tigaiga.

Type of bearing: as indicated above, it is fully remontant comparable to the varieties Brighton and Sans Rivale, but it also produces well in the Spring.

PLANTS (A) Overall size: Medium globose.

(B) General plant habit:

1. *Preferred time of planting (in Soings En Sologne France).*—either September-October in fresh plants, production occuring end of June to October. or April-May in refrigerated plants, production occuring July to October.
2. *Plant habit.*—Flat.
3. *Plant density.*—Medium.
4. *Plant vigor.*—Medium. The plant is less sensitive to parasites than Selva (ph. cactorum).

(C) Leaves:

1. *Size.*—Medium. With mature leaves being approximately 5.5 cm wide, smaller than those of Selva.
2. *Shape.*—Longer than wide.
3. *Color.*—Upper surface medium green, Green Group 137A of The Royal Horticultural Society Colour Chart. Adult leaves are darker green than Selva, same green as Addie. Same coloration from bottom to tip. The color of the lower leaf surface is Green Group 138B of The Royal Horticultural Society Colour Chart.
4. *Growth habit.*—Leaflets as half upright as Selva.
5. *Leaf cross section.*—Slightly convex.
6. *Leaf blistering.*—Medium, shape less blistering than that of Selva.
7. *Terminal leaflet.*—Longer than broad. Shape of base: Acute. Shape of Tip: Obtuse. The length of its terminal leaflet is greater than its breadth, and its base angle is nearly at a right angle, both similar to the variety Elista.
8. *Petiole.*—Position of hairs: Identical as Selva. Diameter of petiole: 1.5 to 2.5 mm. Width of petiole: 14 to 21 cm. Color: Green Group 138C of The Royal Horticultural Society Colour Chart. The pose of its hairs is outwards comparable to the varieties Direktor Paul Wallbaum and Cambridge Favorite.
9. *Stipule.*—Anthocyanin coloration light green with few longitudinal pink streakings.
10. *Stolons.*—High anthocyanin coloration. Very numerous stolons, with medium and smaller diameter than Selva. Pubescence: Weak.

INFLORESCENCE (A) Size and shape: Medium, smaller than Selva. Petals longer than broad with obtuse shape of the bottom.

(B) Peduncules: Thinner than that of Selva.

(C) Pedicel: Thin and medium size, with upward hairs.

(D) Abundance: High density, higher than Selva.

(E) Color: White.

(F) Anther and pollen production: Good production, higher than that of Selva.

(G) Calix size: Slightly smaller than that of Selva.

(H) Position relative of foliage: Beneath.

(I) Flower size: Medium.

(J) Size of calyx relative to selva: Smaller.

(K) Size of inner calyx relative to outer: Same size.

(L) Spacing of petals: Free.

(M) Petal length/width ratio: As long as wide.

(N) Time of flowering (50% of plants at first flower): Long flowering. The fruit is approximately level with the foliage comparable to the varieties Astino and Cambridge Favorite.

Ancestry: as indicated above, it was obtained as a seedling from the parent varieties (Gento × Ostara) × (Red Gauntlet × Korona).

Reproduction: as indicated above the new variety of strawberry was reproduced by the applicant by stolen vegetative multiplication. The color of the seeds is 17B of the yellow-orange group of The Royal Horticultural Society Colour Chart.

Having described the strawberry of my new variety, I claim:

1. A new and distinctive variety of strawberry, substantially as described and illustrated herein, being derived by hybridization from (Gento × Ostara) × (Red Gauntlet × Korona) and distinguished both being remontant and having strong Spring production, and by its scent which is that of wild strawberries.

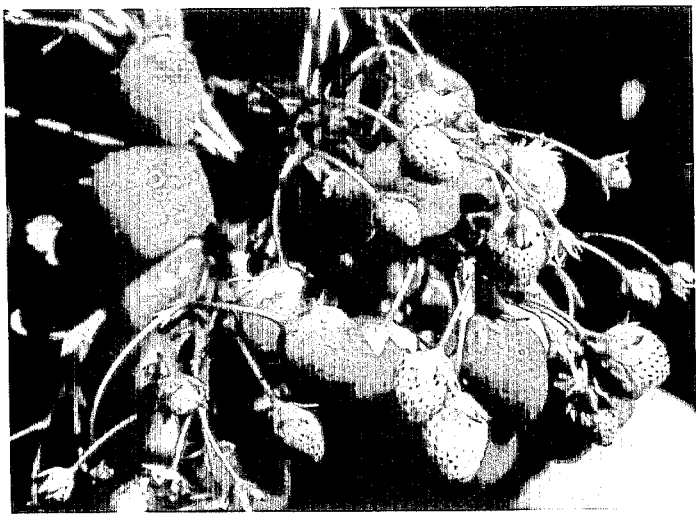
FIG. 2
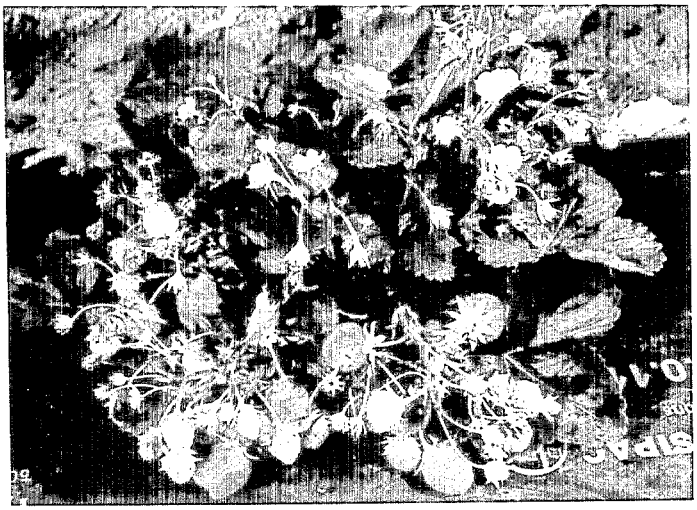

* * * * *